United States Patent [19]

Christensen

[11] Patent Number: 5,662,922

[45] Date of Patent: Sep. 2, 1997

[54] IRON-CONTAINING COMPOSITION FOR THE PREVENTION OF ANAEMIA AND A METHOD FOR PRODUCING THE COMPOSITION

[76] Inventor: Børge Holm Christensen, Odinshøjvej 116, DK-3140 Ålsgaarde, Denmark

[21] Appl. No.: 590,069

[22] Filed: Jan. 17, 1996

Related U.S. Application Data

[63] Continuation of Ser. No. 244,769, filed as PCT/DK93/00017, Jan. 20, 1993, abandoned.

[30] Foreign Application Priority Data

Jan. 20, 1992 [DK] Denmark ................................. 0064/92
Dec. 17, 1992 [WO] WIPO ..................... PCT/DK92/00384

[51] Int. Cl.$^6$ ........................ A23K 1/18; A61K 9/14; A61K 33/26
[52] U.S. Cl. ..................... 424/438; 424/489; 424/490; 424/491; 424/499; 424/646; 424/647; 424/648
[58] Field of Search .................. 424/438, 489, 424/490, 491, 646, 647, 648

[56] References Cited

U.S. PATENT DOCUMENTS

| 3,907,983 | 9/1975 | Seth .......................................... 424/35 |
| 4,752,479 | 6/1988 | Briggs et al. ......................... 424/472 |
| 5,075,138 | 12/1991 | Tanaka et al. .......................... 427/213 |
| 5,096,744 | 3/1992 | Takei et al. ............................. 427/213 |
| 5,100,509 | 3/1992 | Pisecky et al. ......................... 159/4.2 |
| 5,356,625 | 10/1994 | Ying ....................................... 424/94.1 |

FOREIGN PATENT DOCUMENTS

| 0378498 | 7/1990 | European Pat. Off. .......... B01D 1/18 |
| 0406903 | 1/1991 | European Pat. Off. .......... B01J 2/04 |
| 0423701 | 4/1991 | European Pat. Off. .......... B01J 2/00 |
| 136101 | 8/1977 | Germany ....................... A61K 33/26 |
| 1322102 | 4/1973 | United Kingdom .......... A61K 27/00 |
| 1409468 | 10/1975 | United Kingdom ............. B05D 1/02 |
| 1465781 | 3/1977 | United Kingdom ............. A61K 9/14 |

OTHER PUBLICATIONS

Search Report in corresponding International Application No. PCT/DK92/00384 (mailed 15 Mar. 1993).

Search Report in corresponding International Application No. PCT/DK93/00017 (mailed 03 May 1993).

Dialog Accession No. 00824871, WPI Accession No. 90-135712/18 (Snow Brand Milk Poducts), "Iron oasein preparation, useful in treatment of anaemia— by reacting", JP 2083400, publ. 900323.

Olsen: Zeitschrift fur Lebensmittel-Technologie und Verfahrenstechnik, 1983, vol. 34, issue 5 ["Manufacture of New Protein Products for Food Use from Slaughterhouse Blood"; Translation Only].

*Primary Examiner*—Gollamudi S. Kishore
*Attorney, Agent, or Firm*—Fish & Richardson P.C.

[57] ABSTRACT

An oral composition for the prevention of anaemia, comprising highly bioavailable iron and an amino acid-containing ingredient which composition may be ingested voluntarily by a suckling animal in sufficient amounts to maintain a physiologically normal blood composition of the animal, a spray-drying method of manufacturing such a composition comprising an inner core coated with a continuous layer comprising the amino acid-containing ingredient.

55 Claims, 4 Drawing Sheets

5,662,922

IRON-CONTAINING COMPOSITION FOR THE PREVENTION OF ANAEMIA AND A METHOD FOR PRODUCING THE COMPOSITION

This is a continuation of application Ser. No. 08/244,769, filed Jul. 15, 1994, now abandoned, which is a U.S. National application of PCT/DK93/00017, filed Jan. 20, 1993.

FIELD OF THE INVENTION

The present invention relates to the prevention and treatment of anaemic conditions in animals and humans and there is provided an oral composition containing a compound containing iron in a highly bioavailable form which composition has a palatability allowing it to be ingested voluntarily by newborn, suckling individuals in amounts sufficient to cover their physiological requirements for iron. The composition according to the invention may also include substances such as dietary fiber-containing ingredients which prevent or cure diarrhoea including scouring in young animals. Furthermore there is provided a method of producing an iron-containing composition according to the invention.

TECHNICAL BACKGROUND AND PRIOR ART

Anaemic conditions may occur as a result of losses of blood from an individual or as a result of insufficient supply of bioavailable iron in the diet. In this respect, a particular problem exists in the pig industry. Newborn piglets have a total body reservoir of iron which is about 50 mg. During the first 2–3 weeks of life (the suckling period) their weight gain is so rapid that the daily requirement for iron is about 7–10 mg in order to maintain a physiologically normal level of haemoglobin in their blood, i.e. about 90–120 g per 1. However, the daily supply of iron from the sow's milk is only about 1 mg and inevitably, a serious and often fatal, anaemic condition will occur within a few days after birth, if a supplementary iron supply is not provided.

Presently, such a supplementary supply of iron is normally provided by giving newborn piglets an injection of an iron-containing substance such as an iron dextran. Obviously, this method of supplying iron is very labour-consuming and in addition it involves a risk of spreading infectious microorganisms via the injection needle and of causing a stress condition in the animals.

It is therefore not surprising that several attempts have been made to provide iron-containing compositions which by oral administration to suckling piglets might supplement their insufficient supply of iron.

A general problem associated with oral administration to suckling animals of iron-containing compositions is the fact that their energy requirements is substantially covered via the mother's milk and hence they show no willingness to ingest more than a few grammes of solid sources of nutrients and in addition, suckling animals are extremely selective with regard to which solid materials they are willing to ingest.

Sources of iron in oral compositions may be organic or inorganic iron salts or compounds containing chelated iron or complex-bound iron ions. When selecting a suitable iron source for an oral composition, several factors must be taken into account. Whereas it may be advantageous to include an iron source with a high solubility and hence a high degree of bioavailability, at the conditions prevailing in the gastrointestinal tract in order to provide a required dosage at a low amount of the iron-containing composition, such a high solubility may at the same time render the composition so unpalatable that a voluntary ingestion in sufficient amounts by suckling animals, is not obtainable.

Alternatively, it may be attempted to include an iron source having a low solubility and a low degree of bioavailability under gastrointestinal conditions, including those of the oral cavity, whereby the iron-containing composition might become more palatable. In general, however, such an approach would require the administration of amounts of the iron-containing composition exceeding those which may be voluntarily ingested by suckling animals in order to provide a physiologically sufficient iron dosage. In addition, even compositions containing such sparingly soluble iron compounds may not have an acceptable palatability for the suckling animals.

In DE 21 11 638 is disclosed a composition containing iron polysaccharide complexes which is recommended for oral administration to suckling piglets during the first day of life. However, the composition has to be administered by introduction of the composition into the oral cavity in the form of a suspension (by use of a pistol), tablets, capsules, a paste or an aerosol.

There has also been introduced solid iron-containing compositions, e.g. containing ferrous fumarate, which may be ingested voluntarily by suckling animals. However, these known compositions contain iron which is in a form where less than 10% is absorbable and furthermore, in order to provide these known compositions in a sufficiently palatable form, it is required to incorporate relatively low concentrations of iron, such as 10 wt %. Accordingly, a suckling piglet must ingest about 80 grammes during the first two weeks of life in order to avoid anaemia. A number of suckling piglets may not be willing to ingest such a high amount of the composition.

In this context, it is also likely that the requirement to administer the above rather high amounts of an oral iron-supplementing composition is due to an inappropriately large particle size of the selected iron compound. It is known that the iron bioavailability, i.e. the proportion of the iron which can be absorbed from the intestinal mucosal membranes, depends on several factors including the intestinal pH and the particle size. In suckling piglets, the intestinal pH is typically in the range of 4.5 to 6.5. Within this pH range, the solubility of several organic iron compounds including ferrous fumarate is relatively low. Therefore, the incorporation of sparingly soluble iron salts in the form of large particles may result in a low bioavailability of iron in suckling animals.

This problem of reduced bioavailability may be solved by providing the iron in the form of compounds having a small particle size. However, the use of ferrous compounds which are preferred since their bioavailability is generally higher than that of corresponding ferric compounds as small particles in the form of small particles gives rise to a new problem, viz. an acceleration of oxidation of the ferrous compound to ferric compound.

As an alternative to the above direct oral administration to suckling animals of iron-containing compositions it has been suggested to supply a solution of an organic iron compound via automated drinking systems and it has been found that adequate amounts of iron may be taken up by the animals via this route of administration. However, it is required to clean the drinking systems on a daily basis and besides, there is a considerable waste of the iron-containing preparation which may add unacceptably to the costs of such an administration.

It is obvious from the above that a need exists to provide a solid iron-containing composition for the prevention and treatment of anaemic conditions, in particular in suckling animals, which can be administered orally without any manipulation of individual animals and which cost-effectively secures a physiologically normal haemoglobin concentration during periods where the normal dietary iron supply is inadequate.

The present invention provides such an oral iron-containing composition which comprises the iron in a highly bioavailable form and which provides the iron in a palatable form so as to allow the composition to be voluntarily ingested by suckling animals including piglets, in sufficient amounts to maintain the physiologically normal level of haemoglobin.

SUMMARY OF THE INVENTION

Accordingly, the present invention relates in a first aspect to a composition containing gastrointestinally absorbable iron, comprising 0.1 to 25 wt % of elemental iron and 1 to 99 wt % of an amino acid-containing ingredient, the composition being in the form of a free-flowing powder of particles comprising a continuous coating layer containing the amino acid-containing ingredient and an inner core surrounded by the coating layer.

In a further aspect, the present invention pertains to a method of producing a free-flowing powdered iron-containing composition comprising particles of an inner core carrier material coated with a continuous layer of a coating composition comprising an amino acid-containing ingredient, the method comprising (i) preparing a liquid coating composition comprising an amino acid-containing ingredient in an amount in the range of 1 to 99 wt %, calculated on the iron-containing composition, (ii) providing a particulate carrier material having an average particle size being in the range of 1 µm to 100 µm, (iii) adding to the coating composition and/or the inner core carrier material an iron compound in an amount providing a content of elemental iron which is in the range of 0.1 to 25 wt %, calculated on the iron-containing composition, (iv) supplying the coating composition in liquid form to the atomizing means of a spray-drying plant comprising a spray-drying chamber, and atomizing the liquid coating composition into a flow of droplets, (v) supplying a flow of transport gas comprising particles of the carrier material dispersed therein to the spray-drying chamber separately from the coating composition, (vi) supplying a flow of drying gas to the chamber at a temperature which tends to solidify the liquid coating composition, (vii) allowing droplets in the flow of liquid droplets of the coating composition to collide with the particles of the carrier material dispersed in the transport gas, the direction and rate of flow of the transport gas being adapted to substantially prevent contact between on one hand the drying gas and on the other hand the droplets, so that the liquid coating composition, before any substantial drying thereof, will form a substantially continuous liquid layer on the carrier material particles, (viii) then allowing the thus applied continuous coating layer on the particles to at least partially dry by contact with the drying gas, and (ix) withdrawing the coated particles from the spray-drying chamber.

In a still further aspect, the invention provides a method of dietetically supplying iron to an individual suffering from anaemia, comprising administering to said individual the composition as defined herein in an amount and for a period of time which results in a concentration of haemoglobin in the blood of the individual of at least 90 g per l.

DETAILED DISCLOSURE OF THE INVENTION

As it is mentioned above, the present invention provides a free-flowing powdered composition containing gastrointestinally absorbable iron. The composition is generally suitable as a dietary iron supplementation means in individuals suffering from an anaemic condition, but it is particularly useful in newborn, suckling animals such as piglets as an easily administrable iron supplement source. The composition is preferably provided as particles having an average size which is at the most 1 mm such as at the most 0.5 mm.

The source of elemental iron may be any iron compound which when present in the composition as defined herein and administered as defined below, results in the maintenance of a physiologically normal haemoglobin of an animal to which it is administered. In the present context, a suitable iron compound may be selected from an organic iron salt, an inorganic iron salt and a compound in which the iron is chelated or present in a complex-bound form. Although ferrous compounds may be preferred due to a higher bioavailability relative to ferric compounds, the latter group of compounds may also be suitable. Inorganic compounds which may be suitable include as examples iron salts of hydrochloric and sulphuric acid.

In accordance with this invention, any organic iron compound which has the above effect may be selected. In preferred embodiments, the composition comprises an organic iron compound which preferably may be one selected from a formate, an acetate, a propionate, a fumarate, a lactate, a citrate, a succinate, a fatty acid salt of iron, an amino acid salt of iron including glutamate or there may be used a mixture of two or more of these salts. Other useful iron-containing substances include substances wherein the iron is complex-bound to a carbohydrate moiety such as a dextran, and haeme which is the iron-containing prostestic group found in haemoglobin and myoglobin and which may be obtained from these proteins by removing the globin moiety. As it has been mentioned, ferrous compounds are generally more preferred than ferric compounds, since ferrous compounds are more readily absorbed from the intestines.

Commercially available qualities of organic iron compounds may be in the form of relatively coarse particles. As it is mentioned above, iron salts such as e.g. ferrous fumarate which at the pH conditions prevailing in the gastrointestinal tract of suckling animals are sparingly soluble may have an unacceptably low bioavailability when provided as large particles, i.e. particles of a size exceeding 50 µm. Accordingly, in preferred embodiments the present composition may contain an organic iron salt which is in the form of particles of an average size which is at the most 50 µm, such as at the most 30 µm and preferably at the most 10 µm.

In the present context, one particularly useful and economically feasible iron salt is ferrous fumarate. Commercially available grades of this salt, however, may be in the form of particles, the average size of which is considerably larger than 50 µm. Therefore, when ferrous fumarate is selected as the organic iron salt, an initial step of preparing this salt in a finely grained or form is advantageously included in the preparation of the composition. This is conveniently carried out based on the process disclosed in U.S. Pat. No. 3,478,073 according to which an aqueous mixture of fumaric acid and ferrous hydroxide is reacted under conditions where the precipitation of ferrous fumarate results in the formation of fine particles of the above defined size.

An other suitable and economically feasible organic iron source is ferrous formate which in contrast to ferrous fumarate is readily soluble. It has not hitherto been possible to apply this useful iron source in sufficient amounts in oral iron supplementing compositions for suckling animals due to the adverse taste of the dissolved salt. However, when ferrous formate is contained in the present composition, the dissolution of the salt in the oral cavity is avoided or retarded and accordingly, suckling animals may be willing to ingest a composition according to the present invention, in a sufficient amount to cover their need for iron, even if the iron salt is ferrous formate.

In certain preferred embodiments of the present composition, the iron is supplied in the form of salts of amino acids such as e.g. glutamates, or as iron bound to peptides. A mixed amino acid iron salt may thus be prepared by mixing a water soluble iron salt with a hydrolysate of protein whereby amino acid salts and salts of peptides are formed.

As it is mentioned above, the present composition has a content of elemental iron which is in the range of 0.1 to 25 wt %, calculated on the composition. The required amount of the iron-containing compound depends i.a. on the iron content of the compound, the solubility of the compound under the conditions prevailing in the gastrointestinal tract and the particle size in which the compound is provided.

From a cost point of view it is advantageous to select an iron compound with a high content of iron. As one example, ferrous chloride has an iron content of about 65 wt %. Among organic iron salts, a particularly high content of iron is found in ferrous formate (38 wt %), but also ferrous acetate, fumarate, succinate and malate have a high iron content (32–33 wt %). Ferrous glutamate has an iron content of about 28 wt % and a mixture of amino acid salts prepared as mentioned above may typically have an iron content of about 20 wt %.

The iron-containing compound is preferably one which, when present in the gastrointestinal tract has a high degree of bioavailability. Accordingly, when the iron source is an organic iron compound, a bioavailability which is at least 5% is preferred, although one having a bioavailability of at least 10% is more preferred. In particularly preferred embodiments, the organic iron salt has a bioavailability of at least 20%, such as at least 25%. When the iron source is an inorganic iron compound the bioavailability may preferably be at least 25%, more preferably at least 50% and most preferably at least 90%.

In preferred embodiments of the composition according to the present invention, the content of iron is in the range of 2 to 20 wt %, and even more preferably in the range of 3 to 10 wt %.

An essential characteristic of the present composition is that it has a palatability which allows for voluntary uptake by suckling animals in amounts providing a dosage which is sufficient to provide adequate iron supplementation when administered as defined above. This characteristic is e.g. achieved by providing a dry composition comprising the iron compound embedded in or coated by an amino acid containing ingredient, the content of which is in the range of 1 to 99 wt %, calculated on the composition. As it has been mentioned above, ferrous iron e.g. when contained in organic compounds in the form of microscopic particles as defined above are prone to oxidation to the less bioavailable ferric iron. It has been found that such an oxidation may be significantly avoided by incorporating the organic iron compound into the amino acid containing ingredient-containing composition. It will be understood that ferrous iron contained in inorganic compounds will also be prone to oxidation to ferric iron.

Furthermore, this incorporation of iron serves the advantageous purpose of protecting readily soluble iron compounds from rapid dissolution in the oral cavity or further down in the gastrointestinal tract. It is known that the administration to a newly born animal of an iron salt which is readily soluble in the gastrointestinal tract may have a toxic or even lethal effect. Assumingly, this effect is due to absorption of more iron than the iron-transporting blood component transferrin is capable of binding. It has been found that the present iron composition can be administered to suckling animals even during the first days of life without any toxic effect.

A further significant advantage may be obtained by the provision of the iron compound embedded in or coated by an amino acid-containing ingredient in the form of a mixture of amino acids and peptides e.g. as a protein hydrolysate, since such low molecular nitrogen compounds may enhance the intestinal absorption of iron significantly. In addition to these advantages of using a protein hydrolysate in the present composition, the hydrolysate may also provide a dietetically valuable source of amino acids for the individuals to which the composition is administered.

The amino acid containing ingredient may be an animal or vegetable protein or it may be derived from animal or vegetable protein starting materials, although animal proteins may generally be more preferred due to their higher content of essential amino acids as compared to vegetable proteins. However, an amino acid containing ingredient which is one having a dietetically less optimal amino acid composition may be used, preferably in connection with the addition to the composition of a supplement of essential amino acids including lysine, methionine, threonine and tryptophane. Such a supplementation may also be required when an animal protein is used as the amino acid-containing ingredient or as starting material therefor, e.g. when the composition is intended for use in a suckling animal. In the present context, examples of suitable proteins include blood, haemoglobin, myoglobin, milk proteins including caseins and whey proteins, soy protein, leguminous seed proteins, meat and bone meal and fish protein in the form of fish meal. Such proteins may be used as the native proteins or they may be in the form of partially hydrolysed proteins.

One particularly useful amino acid-containing ingredient may be a protein hydrolysate including a hydrolysate of haemoglobin. Haemoglobin is available from animal slaughtering in large quantities at an acceptable cost level. A haemoglobin hydrolysate also provides an additional source of iron in a form which is generally considered to be highly bioavailable. It was surprisingly found during the experimentation leading to the present invention that the feeding to suckling piglets of a milk replacement product containing non-hydrolysed haemoglobin, in an amount which should provide an adequate iron supply, resulted in the development of anaemia in the piglets. It was hypothesized that this lack of utilization of haemoglobin iron might be a consequence of the deficiency in suckling animals of digestive enzymes capable of degrading non-milk proteins. This hypothesis was verified by carrying out a study in which native haemoglobin in the milk replacer was replaced by haemoglobin subjected to a partial enzymatic degradation. Feeding of the thus altered milk replacer to suckling piglets resulted in the maintenance of a physiologically normal level of haemoglobin.

Accordingly, in one advantageous embodiment of the present invention the amino acid-containing ingredient is partially hydrolysed haemoglobin. As an example, hydrolysed haemoglobin may be obtained by treating haemoglobin with an alkaline protease such as Carlsberg subtilisin at a temperature in the range of 50° to 70° C. for 1 to 8 hours to provide a hydrolysate of haemoglobin in which at least 5% of the peptide bonds are hydrolysed, such as e.g. at least 10%. Other suitable proteolytically active enzymes include as examples trypsin, pepsin, chymosin and papain may in accordance with the invention, be used. Acid or alkaline hydrolysis may be used as well.

The content of the amino acid-containing ingredient in the composition is preferably in the range of 5 to 30 wt %, calculated on the composition, such as in the range of 10 to 25 wt %.

In accordance with the present invention it may be advantageous to incorporate a fatty acid-containing substance in the coating layer of the composition in an amount which is in the range of 1 to 50 wt %, calculated on the composition. Preferably, the amount of fatty acid-containing substance is in the range of 5 to 20 wt %, calculated on the composition. It is contemplated that the incorporation of a suitable fatty acid-containing substance in the composition may confer improved oxygen barrier characteristics to the composition by providing a coherent and continuous structure when the composition is dried. Furthermore, it is considered that the fatty acid-containing substance contributes to the prevention of an undesired oral cavity dissolution of the ferrous compound.

Preferred fatty acid-containing substances are substances which have a high degree of digestibility including as examples rendered lard, milk fat, hydrogenated vegetable oils and tallow. It is also contemplated that mixtures of fatty acid substances with melting point above ambient temperature with substances having melting point below this temperature may be useful. Such low melting point substances include vegetable and marine animal oils such as fish oil having a high content of n-3 unsaturated fatty acids. In one preferred embodiment, the composition is an emulsified mixture of an amino acid-containing ingredient such as hydrolysed protein and the fatty acid-containing substance into which the iron compound and optionally one or more of the further ingredients as mentioned below may be mixed. In order to enhance the emulsification, a suitable surface-active emulsifying agent may be added. Suitable emulsifying agents may be selected from commercial food grade emulsifying agents such as fatty acid esters or lecithin.

The iron-containing composition as defined herein may, in addition to those ingredients mentioned above contain at least one further ingredient. Such further ingredients include dietary fiber-containing ingredients, flavouring agents, vitamins, micronutrients, electrolytes, carbohydrates, bacterial cultures, enzymes, alkaline substances or acids. It may thus be particularly interesting to include one or more beneficial bacterial cultures having a growth promoting effect and/or a disease-preventing effect. In this context, useful bacteria may be Bacillus spp which produce exoenzymes capable of degrading nutrient components such as proteins, polysaccharides or fat. Other useful bacteria may be lactic acid-producing organisms such as Lactobacillus spp, Lactococcus spp, Bifidobacterium spp or Streptococcus spp. Interesting enzymes may be ones which degrade proteins (proteases), polysaccharides including starch and cellulose (amylases, cellulases) and/or fatty acid substances (lipases). Supplementation of the composition with such enzymes maybe useful in compositions intended for suckling and weaning animals due to the above-mentioned deficiency in such animals of digestive enzymes capable of degrading the above macromolecules.

The present composition is typically provided in the form of a free-flowing powder having an average particle size which is at the most 1000 μm, e.g. in the range of 10 to 500 μm, preferably in the range of 50 to 250 μm such as e.g. in the range of 100 to 200 μm. In certain useful embodiments the composition may be one wherein a plurality of primary particles as defined herein are agglomerated.

In farm animal production diarrhoea or scouring in young animals is an other serious problem which is presently prevented or treated by the use of antibiotics. However, a widespread use of antibiotic's in animals is associated with a strongly undesirable selection of antibiotic resistant bacteria which may be transferred to humans or healthy animals. Therefore, alternative means of prevention of scouring is needed. One known method is the administration of dietary fiber-containing compositions to young animals. In this context, the term "dietary fiber" is used to designate carbohydrate moieties which are not degradable by animal or human digestive enzymes. For the present invention, pectin-containing substances are presently considered to be particularly useful.

However, the use of such beneficial dietary fiber-containing compositions in suckling animals who are particularly prone to gastrointestinal infection is seriously restricted by the fact that these animals are not willing to ingest the compositions in the amounts which are required to prevent diarrhoea. It is contemplated that a major reason for this rejection is the readiness with which dietary fibers swell in the oral cavity due to their high water absorption capacity.

It has now been found that this problem may conveniently be circumvented by providing the dietary fiber-containing ingredients in the form of comminuted dietary fiber-containing vegetable particles which are incorporated into the composition as defined herein whereby the swelling in the oral cavity is essentially prevented.

As it has been mentioned above, the composition according to the invention is in the form of particles comprising a continuous coating layer containing the amino acid containing ingredient, surrounding an inner core to provide two-component particles in the form of a free-flowing powder. One advantageous embodiment of the invention may be provided by coating as the inner core, particles of a dietary fiber-containing ingredient with the continuous coating layer.

Suitable dietary fiber-containing substance sources include citrus pulp, beet pulp, potato pulp, fruit peel and apple pomace. These sources may have been subjected to various treatments to increase the content of water soluble dietary fiber. Such treatments include as examples treatments with an acid or an alkaline substance. Other useful dietary fiber-containing ingredients may be selected from leguminous seed fibers including pea fiber and soy bean fiber, plant root or tuber fiber products such as potato fiber and cereal fiber products including as examples, oat and wheat brans.

Furthermore, readily water soluble dietary fiber substances such as carrageenans, vegetable and microbially derived gums including Psyllium seed mucilages, guar gum, gum arabicum, xanthan gum, locust bean gum, and alginates may be used in accordance with the present invention. Accordingly, in one preferred embodiment of the invention the iron-containing composition as defined herein is used as a coating layer surrounding a dietary fiber-containing product comprising 20 wt % dried potato pulp, 54 wt % dried apple pomace, 5 wt % dried citrus pulp, 10 wt % guar gum, 10 wt % Psyllium seeds and 1 wt % betaine hydrochloride.

The content of a dietary fiber-containing ingredient in a composition according the present invention is suitably in the range of 1 to 50 wt % such as in the range of 5 to 30 wt %. In other useful embodiments the inner core being coated as defined above may comprise a mixture of a dietary fiber-containing ingredient and the iron compound.

The weight ratio between the coating layer of the present composition and the inner core which it surrounds may be in the range of 10:90 to 99:1. In preferred embodiments, the weight ratio is in the range of 20:80 to 60:40 such as about 1:1. When the composition is one which is in the form of continuous coating layer surrounding an inner core, the above-mentioned further ingredients may be mixed into the coating layer or they may entirely or partially constitute the inner core.

The administration of a composition as defined herein which is in the form a coating layer surrounding an inner core comprising dietary fiber-containing ingredient may reduce the mortality in suckling animals significantly. It has thus been demonstrated that the mortality rate in suckling piglets to which about 35 g of the composition is administered over a 2 week post partum period may be reduced by about 20% as compared to piglets given an injection of an iron preparation.

An interesting feature of the present composition is the possibility of incorporating herein a relatively high amount of an iron compound having a high content of iron and still obtain a composition which may be ingested voluntarily even by suckling animals. Accordingly, the composition as defined herein is one which when administered as the sole iron source in an amount of at the most 35 g to a piglet during the first two weeks after birth results in a concentration of haemoglobin in the blood of said piglet which is at least 80 g per 1, such as at least 90 g per 1. Experiments have shown that it is even possible to achieve a concentration of haemoglobin which is at least 100 g per 1 such as at least 110 g per 1.

In one preferred embodiment, a composition as defined herein is provided as a free-flowing powder comprising particles having an average size which is in the range of 10 to 500 μm. In an other preferred embodiment the composition is provided in a form where a plurality of such particles form agglomerates. This is obtained by including in the manufacturing process an agglomeration step. In order to achieve the desired agglomeration of the particles it is required that these particles are only dried to an extent where the outer surface has a sticky consistency allowing the agglomeration to occur. In accordance with the invention, the agglomerates may preferably have an average size which is in the range of 20 μm to 1000 μm, such as in the range of 30 μm to 750 μm.

As it will be explained in details below the present product is obtained by the above-defined spray-drying method of producing a free-flowing powdered iron-containing composition in the form of particles of an inner core carrier material coated with a continuous layer containing the amino acid-containing ingredient.

It may be advantageous to provide the coated iron-containing powder according to the method in the form of agglomerates of the thus coated particles. Accordingly, the coating method may in a preferred embodiment be one wherein only partial solidification of the continuous coating layer in the spray-drying chamber is performed, so that the particles with the partially solidified coating will be moderately sticky so that they will tend to form loose agglomerates when contacting each other, and the moderately sticky particles are collected on a bed of an air-penetrable material in the form of loose agglomerates and are further dried on the bed to substantially completely dry the coating layer on the agglomerated particles.

It is a characteristic feature of most aspects of the method of the invention that on the one hand the flow of the transport gas with the particles of the carrier material dispersed therein and on the other hand the flow of the drying gas are directed substantially parallel to each other and are regulated so that they form a substantially distinct interface of a substantially constant shape in a region upstream of and adjacent to the region where the collision between the liquid-droplets and the particles takes place, and normally, the flow of the transport gas with the carrier particles dispersed therein and the flow of the drying gas are regulated so that the substantially distinct interface of a substantially constant shape prevails also in the region where the collision between the liquid droplets and the particles takes place and in some cases also downstream of the region where the collision between the liquid droplets and the particles takes place.

The distinct interface being of substantially constant shape (in this context, "constant" means constant over time; there may be variations in e.g. cross section shape or dimensions along the oath from inlet formation of the interface and downstream may be assessed by any suitable means, e.g., simply visually.

The flow of the drying gas and the flow of the transport gas are normally regulated so that they are both substantially laminar until the particles have been coated with the coating composition.

In particular suitable embodiments, the flow of the transport gas with the carrier particles dispersed therein is conducted in a substantially annular cross-sectional shape around the atomizing means, such as illustrated in the drawings and discussed in greater detail in the following. In particular, the flow of the transport gas with the carrier particles dispersed therein is conducted in a substantially circular cross-sectional shape around the atomizing means, the atomizing means being arranged substantially centrally in the circle.

While the method of the invention may be performed in such a manner that the particles will be substantially dry while air-borne in the spray drying chamber, in which case they can be removed from the spray drying chamber by, e.g., suction and be carried to a cyclone, an important embodiment of the method is one wherein only partial solidification of the substantially continuous coating layer in the spray-drying or spray-cooling chamber is performed, so that the particles with the partially solidified coating will be moderately sticky so that they will tend to form loose agglomerates when contacting each other, and the moderately sticky particles are collected on a bed of an air-penetrable material in the form of loose agglomerates and are further dried on the bed to substantially completely dry the coating layer on the agglomerated particles. Such a bed of air-penetrable material may be a moving bed of a filter cloth, such as in a "Filtermat" plant as described in the following.

It will be understood that the term "spray drying" as herein may designate both a drying by evaporation and a solidification of a molten coating composition by cooling. Thus, the drying gas is either a gas which has a temperature above the temperature of the transport gas, thus substantially drying the coating composition by supplying heat thereto, or a gas which has such a temperature below the temperature of the transport gas that it will result in solidification of the coating composition by cooling.

As will be discussed in greater detail in the following, an important feature of the present invention is that it can be effectively used for coating carrier particles which are of a material which is soluble or swellable in water including as typical examples dietary fiber-containing ingredients.

The discoveries leading to the present invention were arrived at in connection with a thorough investigation of the coating process carried out with a model system consisting of an intensely red coating agent and an almost white powder. By this method, the quality of the coating could be followed directly through microscopy of the final products.

The investigations were concentrated around coating in connection with spray drying. The white powder to be coated consisted of pectin fibres, which swell so quickly upon contact with water that dispersing it in the coating agent was impossible. The coating agent consisted of a red-coloured protein solution, droplets of which are known to shell-dry extremely rapidly.

The investigations showed that even with a small amount of coating composition relative to the powder, a complete coating could be obtained, i.e., no visible white particles could be detected in the red final product prepared according to the invention.

It is believed that the coating composition through its high velocity away from the spraying device displaces a large part of the air molecules in an annular region around the device. Thereby, when the measure according to the present invention are not observed, a vacuum is created which sucks in the drying air. Through the collisions between the coating droplets and the molecules of the drying air, a gradual deceleration of the former takes place with a simultaneous filling of the vacuum. The energy exchange between the hot drying air and the droplets is very intensive in this phase, which results in an almost explosive emission of water molecules from the surface of the droplets. Thereby, the ability of the droplets to spread out on the particle surface quickly becomes diminished which is particularly apparent in operations where a thin layer of coating agent is to be spread over all particles.

The method of the invention solves this problem. It is believed that the powder, dispersed in air, is introduced into the innermost part of the above-mentioned vacuum region, so that the collisions between particles and droplets takes place in an annular region so close around the spraying device that the drying air has not, or only to a small extent, penetrated. Thereby, the dispersion is involved in the atomization process itself, in that the coating agent is flung away from the spraying device in the form of a film which, i.a., through the collisions with gas, such as air, molecules and particles of the dispersion, is split up into fine droplets.

The gas, such as air, used for dispersing the powder should be controlled both with respect to amount and temperature. The amount should be so small that the above-mentioned vacuum region is not filled out. If this happens, white particles will immediately appear in the final product. The temperature should be so low that the properties of the droplets with respect to coating do not deteriorate appreciably.

In the method of the invention, however, the introduction of the dispersion occurs in such a manner that the particles and the droplets form the above-mentioned characteristic flow pattern as long as there is a vacuum in the annular collision region. The part of the flow pattern taken up by the particles are shaped as a sharply defined cylinder, whereas the path taken up by the droplets are shaped like a cone in the case of nozzle spraying and like a disc in the case of centrifugal spraying. The transition between the cylinder and cone/disc is likewise sharply defined. If the supply of dispersion is pushed too high, this transition region starts to become fuzzy and dusty, and in the model system, one will find white particles in the otherwise red product as an indication of incomplete coating.

In coating operations where the coating agent is transferred from a liquid to a solid state through spray cooling, the same principles apply with respect to control of the powder-to-air ratio and of the ratio between the powder dispersion and the coating agent as applies when coating by means of spray drying. On the other hand, the temperature of the air used for dispersing the powder should in this case be so warm that the coating agent does not begin to solidify in the collision region.

Naturally, complete coating requires that there is a sufficient amount of coating agent available to cover the total particle surface. If this is not the case, a small deficiency of coating agent results in a mixture of coated and agglomerated particles, whereas with a larger deficiency of coating agent, a purely agglomerated product is obtained.

The method of the invention has thus proved also to be an effective production method for agglomerated products consisting of partly powdery and partly liquid starting materials.

The supply of an even flow of particles to the collision region may be brought about in different ways depending on whether the coating is to be carried out on spray plants having atomizing wheels or having nozzles.

The supply is most easily solved in spray plants with atomizing wheels, since a preferred embodiment of the supply means consists of a jacket around the conical or cylindrical atomizer housing in suitable distance therefrom, so that the flow of particles dispersed in air is able to pass in the resulting interspace. In a preferred embodiment, the particles are blown tangentially in at the top of the interspace, and the particles will therefore move downward along helical paths to the annular exit opening immediately above the annular collision region. In the preferred embodiment, the tangential inlet is placed in such a manner that the particle flow at the outlet rotates in the opposite direction of the atomizing wheel. In this preferred embodiment, partly a completely uniform supply to the entire annular collision region and partly a maximum relative velocity between particles and droplets at the moment of collision is obtained.

As mentioned above, the advantage of this invention is that evaporation of the coating material by means of the hot air is prevented before the collision between the article to be coated and the coating material.

In comparison with the known techniques of particle coating the presently claimed method of producing a coated particle product involves a number of significant advantages. These advantages include the following:

(i) commercially available spray-drying plants can be used, (ii) the present invention comprises a continuous process which compared to traditional coating methods gives lower production expenses, (iii) the method of the present invention has the advantage on the one hand that the flow of the transport gas with the particles of the carrier material dispersed therein and on the other hand the flow of the drying gas are directed substantially parallel to each other and are regulated so that they form a substantially distinct interface of a substantially constant shape in a region upstream of and adjacent to and also prevails in the region where the collision between the liquid droplets and the particles takes place. When comparing with the known art, e.g. EP 423701, the present invention, in a simple and efficient manner, provides the separation between the coating composition and the droplets of coating composition by regulation of the air-flows, which is an efficient and flexible regulation resulting in a much more efficient and controlled process and total flexibility with respect to the use of conventional spray drying plants, (iv) the present invention makes it possible to coat particles which are water-soluble and have irregular shapes.

A special embodiment of the method of the invention can be characterized as a method for coating powder particles in a spray drying or spray cooling plant with a liquid coating agent, said method comprising (i) dispersing the particles uniformly in an air flow with controlled ratio between powder and air, (ii) conducting the dispersion of powder and air into contact with the coating agent at the innermost part of the annular vacuum region formed through the movement of the coating agent droplets away from the atomizing means and to which region the drying or cooling air is prevented from penetrating, (iii) controlling the amount of the dispersion of powder in air supplied per unit of time in such a manner that it is at any time smaller than the amount required to fill the annular vacuum region, (iv) the control of the ratio between the amount of the dispersion of powder in air and the coating agent being exerted on the basis of visual or instrument recording or the characteristic flow pattern formed by the powder particles immediately prior to and subsequent to the collision with the coating agent droplets, and (v) controlling the temperature of the dispersing air flow independent of the-drying or cooling air so as to delay the initial transition of the liquid coating agent into solid form till after the collision with the powder particles.

BRIEF DESCRIPTION OF THE DRAWING

FIG. 3 shows coating in connection with a spray plant having a conical atomizer housing 36 and an atomizing wheel 37. A jacket 38 is placed at a distance from the atomizing wheel, which ensures a suitable air and particle velocity in the interspace between the atomizer housing and the jacket. Reference numerals 39 and 40 designate the annular collision region.

In plants with nozzle atomization, which normally have several nozzles, the supply means to the individual nozzle consists in the preferred embodiment of a double walled tube where the nozzle and its feed tube are placed at the centre, and where the particles are blown in tangentially into the interspace between the walls the end opposite the nozzle.

Figure 2:
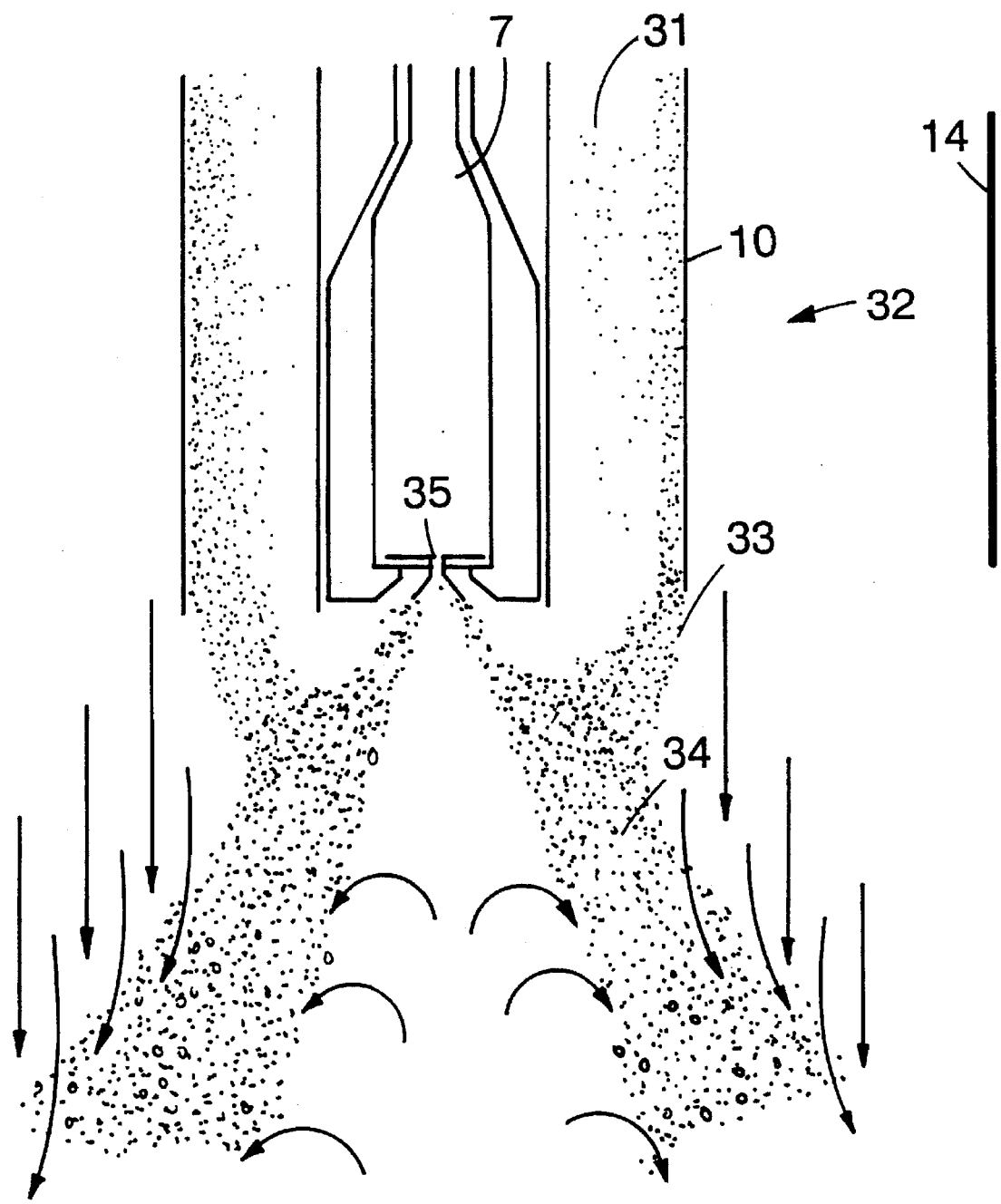
FIG. 2 is a diagram showing coating in connection with a spray plant with nozzle atomization. A nozzle 7 with a perforated disc 35 atomizes a coating agent so that droplets move away from the disc 35. A double walled tube defines an interspace 31 conducting the particle flow to an annular collision region 34.
Figure 3:
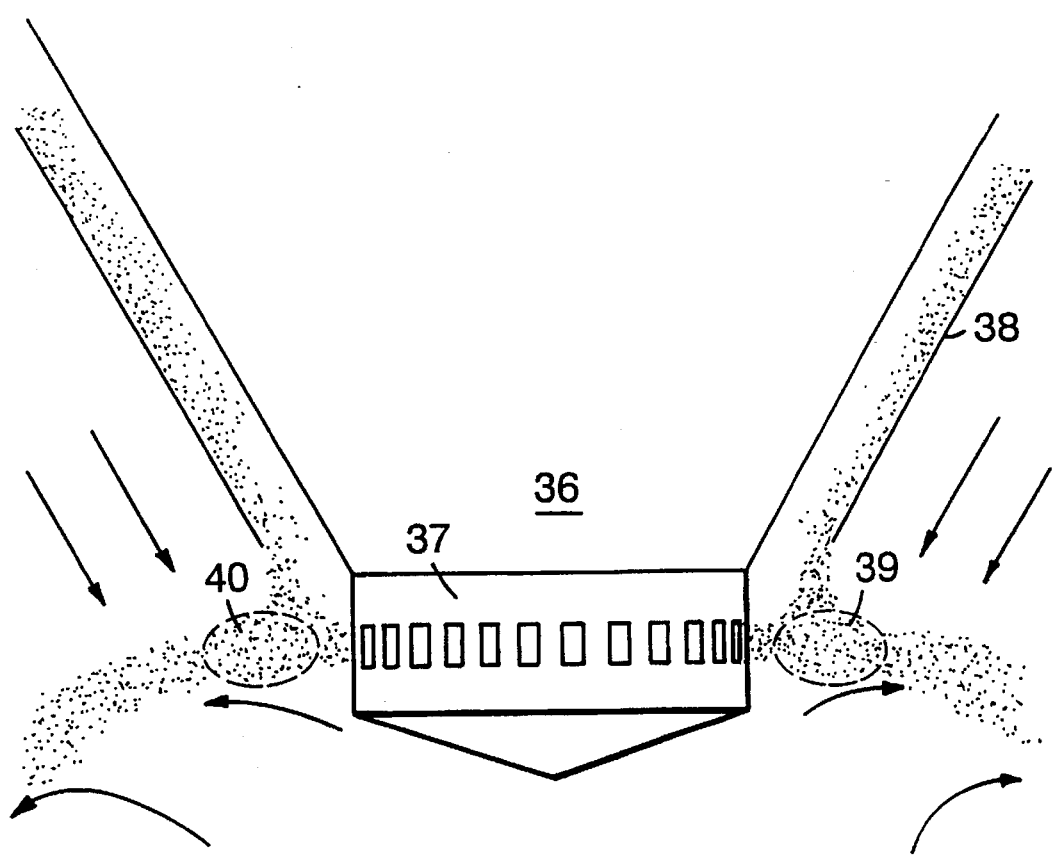
FIG. 3 is a diagram showing coating in a spray plant having a conical atomizer housing 36 and an atomizing wheel 37, and placed at a distance from said atomizing wheel, a jacket 38. Numerals 39 and 40 designate an annular collision region.

FIG. 2 shows coating in connection with a spray plant with nozzle atomization. A nozzle 7 with a perforated disc 35 atomizes the coating agent so that the droplets move away from the disc 35 in paths describing a hollow cone. A double walled tube defines an interspace 31 conducting the particle flow to the annular collision region 34.

In the event of several nozzles, however, this means that the adjusted flow of particles to the spray plant must be divided into a number of equal partial flows to each respective nozzle. In a preferred embodiment, this is done by supplying the adjusted total particle flow into the centre of a centrifugal ventilator which has as many exits as there are nozzles. By giving the exits completely identical shapes, it is ensured that the partial flows of particles to the individual nozzles will be exactly the same.

Figure 4A:
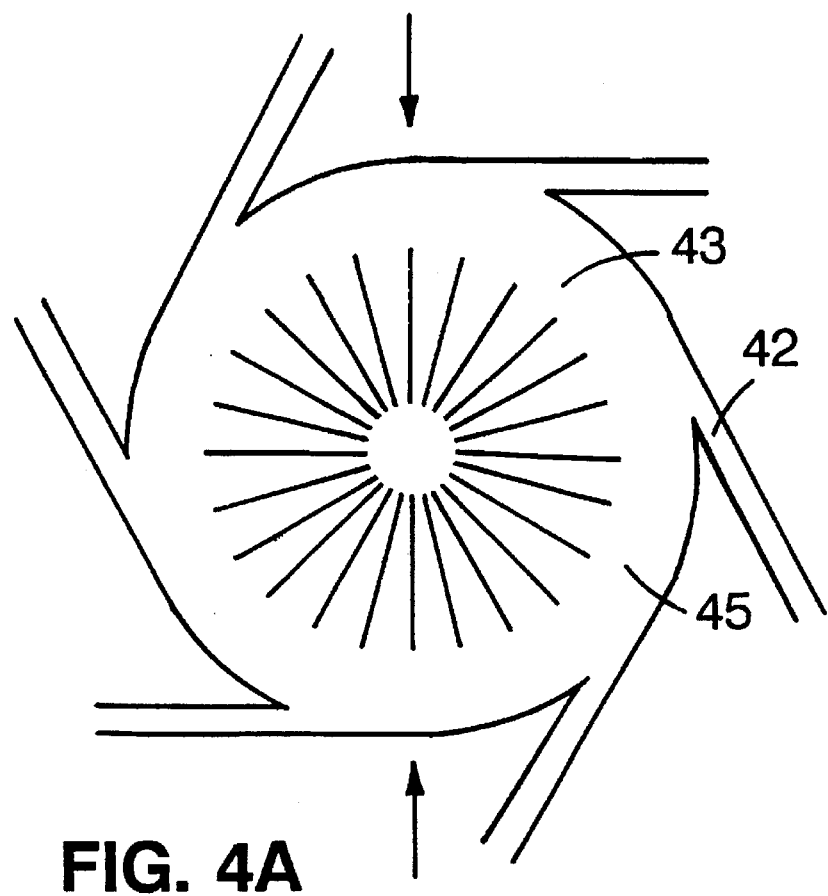
FIGS. 4A and 4B are (top view and cross-section, respectively) diagrams showing a centrifugal ventilator with six exits for dividing a flow of powder into six partial flows. Reference numeral 43 designates a ventilator housing, numeral 42 one of six individual exits, reference numeral 45 designates a ventilator wheel, reference numeral 46 a central inlet for a powder flow and reference numeral 47 an inlet for transport gas.
Figure 4B:
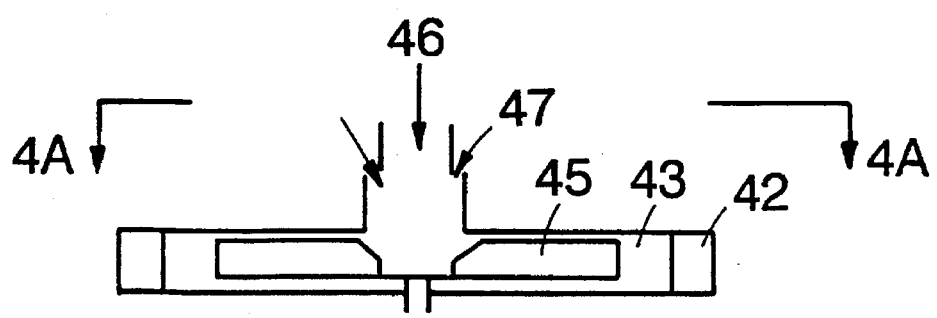

FIG. 4 shows a centrifugal ventilator with 6 exits for dividing a flow of powder into 6 partial flows. Reference numeral 43 designates a ventilator housing, and reference numeral 42 designates one of six identical exits which are arranged in a rotation-Symmetrical manner. Reference numeral 45 designates the ventilator wheel, reference numeral 46 designates the central inlet for the powder flow, and reference numeral 47 designates the inlet for the transport air.

Figure 1:
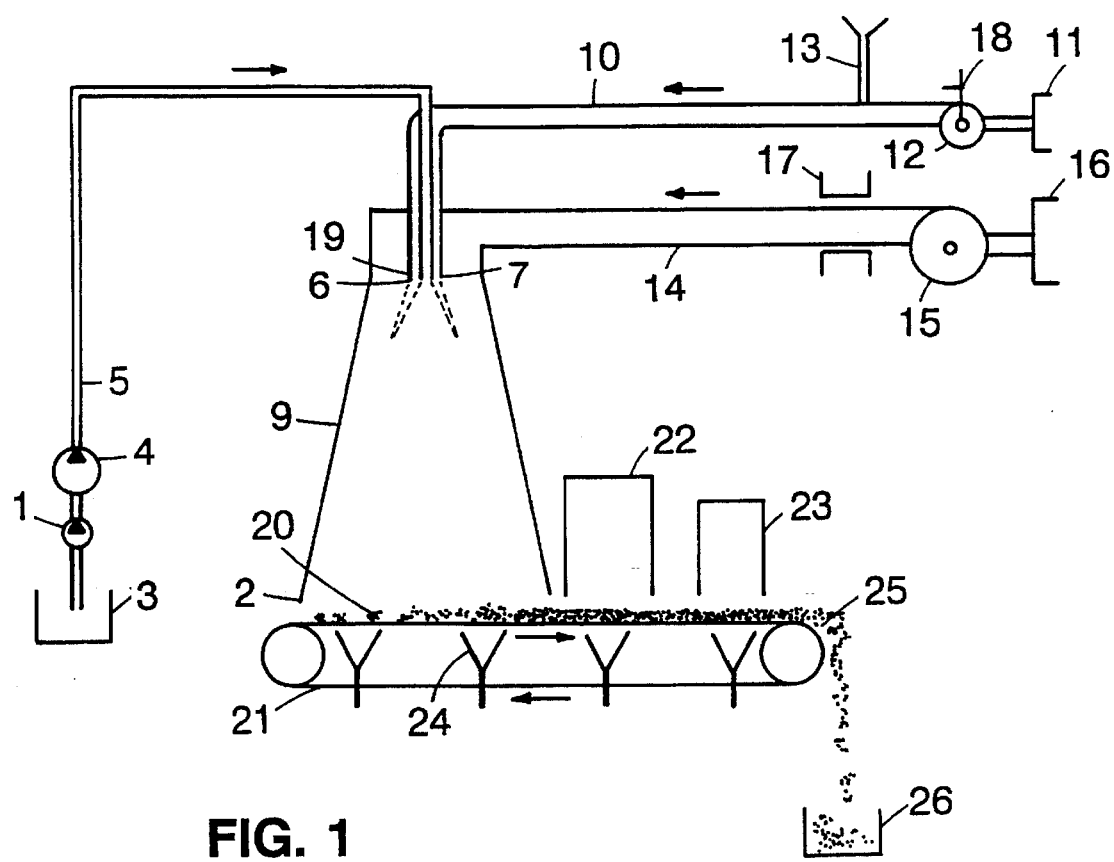
FIG. 1 is an illustration diagramming a conventional filtermat spray-drying or spray-cooling plant.

FIG. 1 diagrammatically illustrates what may be considered as a conventional filtermat spray-drying or spray-cooling plant. This kind of spray-drying or spray-cooling plant may preferably be used when carrying out the method according to the invention. The spray-drying or spray-cooling plant comprises a spray-drying or spray-cooling chamber 9 wherein a carrier material is coated with a coating composition. The spray-drying or spray-cooling plant illustrated in FIG. 1 is provided with nozzle means for atomizing a liquid coating composition in a liquid form. However, a spray-drying or spray-cooling plant having an atomizing wheel for atomizing the liquid coating composition may also be used. The spray-drying or Spray-cooling plant in FIG. 1 could be provided with a number of nozzles, such as 1–24, but to simplify the description the spray-drying or spray-cooling plant in FIG. 1 is only provided with one nozzle.

A coating composition in liquid form is introduced into the spray-drying or spray-cooling chamber 9 through a high-pressure atomizing nozzle 7 (positioned in the upper part, preferably 6–8 m, more preferably 7 m above the bottom of the of the spray-drying or spray-cooling chamber 9) atomizing the liquid coating composition into droplets. The high-pressure atomizing nozzle 7 is fed with the liquid coating composition under pressure via a supply pipe 5. The pressure is generated by a high-pressure feed pump 4 fed by a feeding pump 1 and communicating with a storage 3 containing the liquid coating composition. The spray-drying or spray-cooling chamber 9 has the form of a hollow frustum of a pyramid, with an opening 2 in the bottom, this opening 2 is preferably of 2.2 m and an upper almost circular opening 8, preferably having an inner diameter in the order of 1.2 m. The high-pressure feed pump 4 generating a pressure in the range of 50–400 atm, preferably in the order of 200 atm. The feeding pump 1, preferably generating a pressure in the range of 2–3 atm. The supply pipe 5 is a high-pressure pipe, preferably with an inner diameter in the order of 8 mm.

The particles of the inner core carrier material, to which the droplets of liquid coating composition is applied, are supplied with a flow of a transport gas, preferably air, to the spray-drying or spray-cooling chamber 9 from an inlet 19 communicating with a particle transporting pipe 10. The particles of the carrier material are dispensed from a dosing means 13 into the particle-transporting pipe 10 and air-borne by the flow of transport gas to the inlet 19. The flow of the transport gas is derived by a fan 12 from the atmosphere through an inlet air filter 11.

After coating of the particles in the spray-drying or spray-cooling chamber 9, the air-borne coated particles are brought into contact with a drying or cooling gas, preferably air, in order to solidify the coating at least partly. The drying or cooling air is through a grid 6 supplied from a supply pipe 14 communicating with a fan 15 deriving air from the atmosphere through an inlet air filter 16. The grid provides a minor pressure drop in the drying or cooling air and give a more laminar flow of the drying or cooling air into the spray-drying or spray-cooling chamber 9. Depending on the actual process to be carried out by the spray-drying or spray-cooling plant, the supply pipe 14 may be provided with air-heating means, such as a gas burner, or air-cooling means 17, respectively.

The direction and the rate of flow of the transport gas are adapted by means of a regulator 18, preferably a frequency converter, regulating the flow through the fan 12. This adaptation substantially prevents contact between, on the one hand, the drying gas and, on the other hand, the droplets so that the liquid coating composition, before any substantial drying thereof, will form a substantially continuous-liquid coating layer on the particles.

Normally, the supply of drying gas or cooling gas may be adjusted by regulators not shown in the drawings.

The particles with at least partly solidified coating in the spray-drying or spray-cooling chamber 9 will be moderately sticky so that they will tend to form loose agglomerates 20 when contacting each other on a movable filtermat belt 21 of air-penetrable material in the form of loose agglomerates. The velocity of the filtermat belt 21 is preferably adjustable. The agglomerates 20 are transported by the belt 21 into at least one drying chamber 22 performing a further second drying of the agglomerates 20 and preferably into a cooling chamber 23 for cooling of the agglomerates 20 before leaving the movable filtermat belt 21. The finished agglomerates 20 are transported to a point 25 where the belt returns, the agglomerate here fall into a hopper 26 for optional further processing. The belt may preferably have a length of 10–12 m, and preferably a width of 1.5–2.0 m such as 1.8 m.

Under the movable filtermat belt 21 in positions under the spray-drying or spray-cooling chamber 9, the chamber 22 and the chamber 23, respectively, exhaust chamber 24 connected to adjustable exhausting fans are provided. The exhaust chamber 24 draws the drying or cooling air through the mat of product and the air-penetrable material. The air-penetrable material is preferably of polyester or polypropylene and is preferably of a kind of fabric having small loops in its outer weaver and bigger loops in its inner weaver so as to prevent material from getting stocked in the fabric.

The high-pressure atomizing nozzle 7 used in the spray-drying and spray-cooling plant illustrated in FIG. 1 is preferably a whirl chamber nozzle providing a mist having a hollow cone shape.

The movable filtermat belt 21, the drying chamber 22, the cooling chamber 23, the exhaust chamber 24 and fans 12 and 15 may preferably be parts from a F500 NIRO Filtermat plant.

FIG. 2 illustrates the zone around a high-pressure atomizing nozzle 7 operating in a spray-drying or spray-cooling plant as described in FIG. 1. In this zone, on the one hand, a flow of a transport gas 31 with particles of a carrier material dispersed therein (supplied from a particle-transporting pipe 10) and, on the other hand, a flow of the drying or cooling gas 32 (supplied from a supply pipe 14) are directed substantially parallel to each other and are regulated so that they form a substantially distinct interface of a substantially constant shape in a region 33 upstream of and adjacent to a region 34 in which the collision between the dispensed liquid droplets and the particles takes place. The droplets are dispensed from the high-pressure atomizing nozzle 7 having a disc 35 with a central opening wherefrom the droplets are dispensed in a hollow conical mist.

| | |
|---|---|
| 1 | feeding pump |
| 2 | opening |
| 3 | storage |
| 4 | high-pressure feed pump |
| 5 | supply pipe |
| 6 | grid |
| 7 | high-pressure atomizing-nozzle |
| 8 | cyclone |
| 9 | spray-drying or spray-cooling chamber |
| 10 | particle-transporting pipe |
| 11 | inlet air filter |
| 12 | fan |
| 13 | dosing means for carrier material |
| 14 | supply pipe |
| 15 | fan |
| 16 | inlet air filter |
| 17 | air-heating means or air-cooling means |
| 18 | regulator |
| 19 | inlet for transport gas |
| 20 | agglomerated coated particles |
| 21 | movable filtermat belt |
| 22 | secondary drying or cooling chamber |
| 23 | cooling chamber |
| 24 | exhaust chamber |
| 25 | product release point |
| 26 | hopper |
| ... | |
| 31 | transport gas |
| 32 | drying or cooling gas |
| 33 | collision region |
| 34 | collision region |
| 35 | disc |
| ... | |
| 36 | atomizer housing |
| 37 | atomizing wheel |
| 38 | jacket |
| 39 | collision region |
| 40 | collision region |
| ... | |
| 42 | exit |
| 43 | ventilator housing |
| 45 | ventilator wheel |
| 46 | powder inlet |
| 47 | transport gas inlet |

As mentioned above, the present invention relates in a still further aspect to a method of dietetically supplying iron to an individual suffering from anaemia, comprising administering to the individual a composition as defined herein. The composition is administered in an amount and for a period of time which results in the maintenance of a physiologically acceptable concentration of haemoglobin in the blood. Preferably, the concentration of haemoglobin to be obtained and maintained is at least 90 g per 1 of blood. The method is particularly feasible for the prevention of anaemia in suckling piglets. A suitable iron supplementation regime in suckling piglets is the administration of the present composition to the piglets over a period of two weeks post partum in a total amount of at the most 35 g per piglet. The composition is e.g. administered by scattering it on the floor of the farrowing pen from where it is voluntarily ingested by the piglets. One convenient regime of administration of the composition is to divide the total dosage into six or seven daily dosages which is administered every second day during the period of administration.

It will, however, be understood that the method as defined herein is not limited to use in suckling piglets. Other animals, especially animals on a predominant diet of milk or milk replacer may occasionally have a dietary intake of iron which is not sufficient to secure a physiologically acceptable haemoglobin level. The feeding of the present iron-containing composition may constitute a convenient method of providing an adequate iron supplementation to such animals. The composition may be administered to these animals by incorporating a suitable amount hereof in the milk or milk replacer diet or it can be offered to the animals as a separate feed additive. Furthermore, the method may be used to repair an iron deficiency in humans suffering from anaemia.

The invention is further illustrated in the below Examples:

EXAMPLE 1

Preparation of an iron-containing composition

A liquid mixture comprising the following ingredients was prepared:

|  | Amount | % dry matter |
| --- | --- | --- |
| Hydrolysed haemoglobin | 325.0 kg | 28 |
| Alcalase ™ Food Grade[1] | 0.46 kg | 100 |
| NaOH | 9.9 kg | 27 |
| Rendered lard | 132.0 kg | 100 |
| Panodan ™[2] | 1.32 kg | 100 |
| Ferrous fumarate | 511.0 kg | 27 |
| E vitamin | 0.05 kg | 100 |
| Lysine | 0.82 kg | 100 |
| Methionine | 2.09 kg | 100 |
| Threonine | 1.23 kg | 100 |
| Tryptophane | 0.41 kg | 100 |
| Total weight | 983.78 kg |  |
| Dry matter | 369.84 kg | 37.6 |

[1] Novo Nordisk, containing Subtilisin Carlsberg
[2] A commercial emulsifying agent (Grindsted Products)

The hydrolysed haemoglobin was prepared essentially as described in Olsen, *Zeitschrift für Lebensmittel—Technologie und Verfahrenstechnik*, 1983, vol. 34, issue 5 on the basis of frozen blood cells separated from porcine blood collected under substantially sterile conditions in a slaughterhouse, by centrifugation followed by freezing. The frozen blood cells were thawed by circulation over a heat exchanger to obtain a thawed blood cell suspension having a temperature of about 55° C. which was subsequently subjected to the hydrolysis treatment as follows:

The Alcalase™ Food Grade was added directly to the thawed blood cells in a vessel provided with heating and agitating means and the NaOH were added to the mixture by means of a dosing pump controlled by a pH meter to obtain and maintain a pH in the range of 8.0 to 8.5. The temperature in the reaction mixture was about 55° C. and the reaction time was about 4 hours until a degree of hydrolysis (DH) of 18–20 was obtained.

The ferrous fumarate was derived from a freshly prepared batch prepared substantially in accordance with the method described in U.S. Pat. No. 3,478,073. Initially, 375 kg of dry NaOH in pellets were dissolved under agitation by means of a centrifugal pump in 1200 kg of boiled out water in a 6 m$^3$ tank. 2×500 kg of ferrous sulphate (FeSO$_4$,7H$_2$O) was dissolved in 2×1200 kg of boiled water in a 2 m$^3$ tank and subsequently pumped through a filtration bag by means of a centrifugal pump into the tank containing the NaOH solution to obtain the formation of ferrous hydroxide and sodium sulphate. 450 kg of fumaric acid was added slowly to the 6 m$^3$ tank during agitation by means of a centrifugal pump to obtain a suspension of precipitated ferrous fumarate. This suspended ferrous fumarate precipitate was pumped through a filter to remove particles having a size of more than about 50 μm followed by a decanting step whereby most of the sodium sulphate solution was removed.

The resulting ferrous fumarate slurry containing 30 to 35 wt % of the salt was transferred to a 2 m$^3$ tank and subjected to further decanting followed by returning the resulting slurry to the 6 m$^3$ tank. About 2 m$^3$ of boiled water was added while agitating by means of the centrifugal pump. The decanting step was repeated twice and 511 kg of the thus washed ferrous fumarate slurry having a dry matter content of about 27 wt % was used in the further processing.

An emulsion of the rendered lard (food grade) and the hydrolysed haemoglobin was prepared using the Panodan™ emulsifying agent, by pumping the hydrolysed haemoglobin at a temperature in the range of 45° to 50° C. into a mixing vessel following by pumping the lard, also at a temperature in the range of 45° to 50° C., into the vessel under vigorous agitation, however, without whisking in air. The mixture was emulsified by means of a Greaves™ mixturing equipment for about 10 minutes followed the addition under vigorous agitation of the ferrous fumarate, the E vitamin and the amino acids and the resulting liquid emulsified mixture was transferred to the feeding tank of a high pressure pump.

In a subsequent coating step the resulting liquid iron-containing composition was applied in a spray-drying coating process to the surface of the particles of a dry powdered mixture of the following ingredients, prepared by blending in a Nauta™ blending apparatus:

| Biopect ™[3] | 82.0 kg |
| --- | --- |
| Vitamin mixture | 9.0 kg |

A coating step was then carried out in a spray-drying plant in the following manner using a spray-drying equipment of the type Filtermat™ F500 from Damrow with an evaporation capacity of 500 lbs/hour. This spray-drying equipment comprises a spray drying chamber and an atomizing means in the form of a spray nozzle of type Delavan™ working at a pressure of 150 bar and giving an open hollow cone spray.

The Filtermat™ F500 equipment consisted of the following components:

(i) a spray-drying tower with a square bottom of 2×2 m, the distance from the spray nozzle to the conveyor belt being 7 m, (ii) an application pipe for the particles of the carrier material having a diameter of 12 cm, the pipe being equipped in the centre with an internal pipe having an internal diameter of 8 mm which internal pipe ends in the nozzle, (iii) a Filtermat belt with a width of 1.8 m and a total length of 11 m, the part of the belt receiving the coated powder being 5 m. The Filtermat belt which comprises an air-penetrable filter cloth made of a woven 2-layer polymeric material and woven in a way so that the air-penetrating pores of the upper layer have a smaller diameter than the pores of the bottom layer, (iv) a retention chamber over the Filtermat belt next to the spray tower, (v) a secondary drying chamber next to the retention chamber and (vi) a cooling chamber at the outlet end of the belt.

The drying air in the spray tower had an inlet temperature of about 250° C. and an outlet temperature of about 75° C.

The coating step comprised supplying as a coating composition the above liquid iron salt-containing emulsion to the spray nozzle of the spray-drying equipment and atomizing the liquid coating composition into a flow of droplets followed, supplying a flow of transport gas comprising as a carrier material particles of the above powdered pectin-containing mixture dispersed therein to the spray-drying chamber separately from the coating composition, supplying a flow of drying gas to the chamber at a temperature which tended to solidify the liquid coating composition.

During operation, the equipment was regulated so as to allow droplets in the flow of liquid droplets of the coating composition to collide with the particles of the carrier material dispersed in the transport gas, the direction and rate of flow of the transport gas being adapted so that contact between on one hand the drying gas and on the other hand the droplets was substantially prevented whereby the liquid coating composition, before any substantial drying thereof, formed a substantially continuous liquid layer on the carrier material particles. Subsequently, the thus applied continuous coating layer on the particles were allowed to partially dry by contact with the drying gas.

When discharged from the spray tower the coated particles were further dried in the retention chamber and in the drying chamber of the filter bed by means of air having an inlet temperature of about 75° C. and an outlet temperature of about 60° C. The dried and coated particles were further cooled at ambient temperature.

From the above coating process there was obtained an iron-containing composition in the form of a free-flowing powder comprising agglomerates of primary particles having an average size of about 50 μm in which agglomerates the primary particles were in the form of a continuous coating layer consisting of the dry matter of the above iron salt-containing emulsion surrounding an inner core of the pectin-containing composition. The resulting composition had a content of elemental ferrous-iron of about 9.6 wt % and a content of the pectin-containing composition of about 18 wt %. The weight ratio between the amount of coating layer dry matter and the inner core composition was about 4:1.

EXAMPLE 2

The effect of an iron-containing composition on blood composition and mortality rate in piglets A one-year trial including 950 litters of piglets was carried out under the supervision of the Landsudvalget for Svin (Danish National Committee for Pig Breeding). Half of the litters was offered about 60 g of a product as defined in Example 1 per litter on Mondays, Wednesdays and Fridays during the first two weeks of life. This dosage corresponded to about 33 per pig during the two week test period. The other half of the litters (control) were given 200 mg of iron by an injection on the third day of life of a commercial iron-containing injectable preparation.

The test piglets were willing to ingest all of the composition. At the end of the second and the third week, respectively, blood samples of all piglets were collected and the samples analyzed for the concentration of haemoglobin (g/l) and for the haematocrit value (the percentage of the blood that is cells).

The results of the trial are summarized in Table 1 below:

TABLE 1

| | Concentration of haemoglobin ((g/l) and haematocrit (percent) | | | |
|---|---|---|---|---|
| Age | 2 weeks | | 3 weeks | |
| Group | Injection | Composition | Injection | Composition |
| No. of samples | 80 | 80 | 80 | 80 |
| Haemoglobin | 117 | 117 | 129 | 120 |
| Haematocrit | 40 | 40 | 43 | 40 |

The test litters had an average diarrhoeal frequency of 9.2% during the first week of life whereas the control litters had a corresponding frequency of 10.3%. The mortality rate in test litters during the period from the third day of life and until weaning was 3.9 and the corresponding rate for control litters was 4.7 (p<0.09).

EXAMPLE 3

The effect of an iron-containing composition on blood composition and mortality rate in piglets A trial was carried out over a 3 month period on the commercial pig unit at the Lancashire College of Agriculture and Horticulture. The purpose of the trial was to record the performance of piglets on two different iron supplementation regimes, viz. an injection of 1 ml iron dextran on day 2 of the piglets life (control groups) as compared to an oral supplementation of about 60 grammes of the composition as defined in Example 1 administered as described in Example 2 by scattering the composition on the floor of the littering pen (test groups). A total of 15 litters per treatment were recorded. In total 296 piglets participated The following data were recorded: (1) blood characteristics, measured at both 10 and 21 days of age including haemoglobin concentration, serum iron concentration and haematocrit values and (2) mortality rates.

The results of blood sample analyses (average for all animals) are summarized in Table 2:

TABLE 2

| | Blood characteristics (concentration of haemoglobin, g/l, serum iron, μg/100 ml and haematocrit, percent) | | | |
|---|---|---|---|---|
| Age | 10 days | | 21 days | |
| Group | Injection | Composition | Injection | Composition |
| Haemoglobin | 100 | 107 | 102 | 118 |
| Serum iron | 80 | 167 | 42 | 98 |
| Haematocrit | 32 | 34 | 32 | 37 |

On day 10 the mortality rate was 6.2% in the control group as compared to only 2.7 in the test group. On day 21 the corresponding figures for the period of day 10 to 21 were 2.9 versus 1.4. For the period of day 0 to 21 the mortality rate was 9.0 in the control group versus 4.0 in the test group. This difference is statistically significant (p<0.05).

Based on the results of this trial it can also be concluded that the uptake of iron was superior in the piglets offered the composition of the present invention compared to that of the iron injection (control) piglets at both day 10 and day 21 post partum.

I claim:

1. A composition containing gastrointestinally absorbable iron, comprising 0.1 to 25 wt % of ferrous or ferric iron and 1 to 99 wt % of an amino acid or an amino acid-containing ingredient selected from the group consisting of a milk protein and a partially hydrolyzed protein, the composition being in the form of a free-flowing powder of particles comprising a continuous coating layer containing the amino acid or amino acid-containing ingredient and an inner core surrounded by said coating layer, said inner core comprising at least one component selected from the group consisting of a ferrous iron containing compound and a ferric iron-containing compound, said composition having a palatability to a newborn suckling piglet such that it is ingested voluntarily by said piglet in an amount sufficient to provide adequate iron supplementation.

2. The composition according to claim 1 wherein the particles have an average size which is at the most 1 mm.

3. The composition according to claim 1 wherein the ferrous or ferric iron-containing compound is an organic iron compound.

4. The composition according to claim 3 wherein the organic iron compound contains an anion selected from the group consisting of a fumarate, an acetate, a glutamate, a succinate, a formate, a lactate, a dextran, a propionate, a fatty acid salt of iron, an amino acid salt of iron, and a mixture thereof.

5. The composition according to claim 4 wherein the organic iron compound is ferrous fumarate.

6. The composition according to claim 3 wherein the content of iron is in the range of 3 to 10 wt %.

7. The composition according to claim 3 wherein the organic iron compound is provided in the form of particles of an average size which is at the most 50 μm.

8. The composition according to claim 7 wherein the organic iron compound particles have an average size which is at the most 30 μm.

9. The composition according to claim 1 wherein the partially hydrolyzed protein has a degree of hydrolysis which is at least 5%.

10. The composition according to claim 9 wherein the partially hydrolyzed protein has a degree of hydrolysis which is at least 10%.

11. The composition according to claim 1 wherein the partially hydrolyzed protein is partially hydrolyzed haemoglobin.

12. The composition according to claim 1 wherein the content of the amino acid or amino acid-containing ingredient is in the range of 5 to 30 wt %.

13. The composition according to claim 1 wherein the coating layer further comprises a fatty acid-containing substance is an amount which is in the range of 1 to 50 wt %.

14. The composition according to claim 13 wherein the amount of the fatty acid-containing substance is in the range of 5 to 20 wt %.

15. The composition according to claim 1 wherein the coating layer comprises an emulsified mixture of the amino acid or amino acid-containing ingredient and a fatty acid-containing substance, said fatty acid-containing substance being selected from the group consisting of rendered lard, milk fat, tallow, a vegetable oil and a marine animal oil.

16. The composition according to claim 1 further comprising at least one dietary fiber selected from the group consisting of a pectin, a carrageenan, a vegetable gum a microbially derived gum, and an alginate.

17. The composition according to claim 16 wherein at least 50% of the dietary fiber is soluble in water.

18. The composition according to claim 16 wherein the content of the dietary fiber is in the range of 1 to 50 wt %.

19. The composition according to claim 18 wherein the content of the dietary fiber is in the range of 5 to 30 wt %.

20. The composition according to claim 1 wherein the coating layer further comprises a ferrous or ferric iron-containing compound.

21. The composition according to claim 3 wherein the inner core further comprises a dietary fiber selected from the group consisting of a pectin, a carrageenan, a vegetable or microbially derived gum and an alginate.

22. The composition according to claim 1 wherein the weight ratio between the coating layer and the inner core is in the range of 10:90 to 99:1.

23. The composition according to claim 22 wherein the weight ratio is in the range of 20:80 to 60:40.

24. The composition according to claim 23 wherein the weight ratio is about 1:1.

25. The composition according to claim 1 comprising particles having an average size which is in the range of 10 to 500 μm.

26. The composition according to claim 1 which is in the form of agglomerates formed by agglomerating a plurality of particles during a manufacturing process.

27. The composition according to claim 26 wherein the particle agglomerates have an average size in the range of 20 to 1000 μm.

28. The composition according to claim 27 wherein the particle agglomerates have an average size in the range of 30 to 750 μm.

29. The composition according to claim 1 which, when administered by feeding as the sole iron source in an amount of at the most 35 g to a piglet over the first two weeks after birth, results in a concentration of at least 80 grams per liter of haemoglobin in the blood of said piglet.

30. The composition according to claim 29 which, when administered by feeding as the sole iron source in an amount of at the most 35 g to a piglet over the first two weeks after birth, results in a concentration of at least 90 grams per liter of haemoglobin in the blood of said piglet.

31. A method of producing a free-flowing powdered iron containing composition in the form of particles comprising an inner core material comprising at least one component selected from the group consisting of a ferrous iron-containing compound and a ferric iron-containing compound, said inner core material being coated with a continuous layer of a coating composition comprising an amino acid or an amino acid-containing ingredient selected from the group consisting of a milk protein and a partially hydrolyzed protein, the method comprising the steps of:

(i) preparing said liquid coating composition, (ii) preparing said inner core material having an average particle size in the range of 1 μm to 100 μm, (iii) adding to said coating composition or said inner core material an iron compound in an amount resulting in a content in the composition of ferrous or ferric iron which is in the range of 0.1 to 25 wt %, (iv) supplying the coating composition in liquid form to an atomizing means of a spray-drying plant comprising a spray-drying chamber, and atomizing the liquid coating composition into a flow of droplets, (v) supplying a flow of transport gas comprising particles of the core material dispersed therein to the spray-drying chamber separately from the coating composition, (vi) supplying a flow of drying gas to the chamber at a temperature which tends to solidify the liquid coating composition, (vii) allowing droplets in the flow of liquid droplets of the coating composition to collide with the particles of the core material dispersed in the transport gas, the direction and rate of flow of the transport gas being adapted to substantially prevent contact between the drying gas and the droplets, so that the liquid coating composition, before any substantial drying thereof, will form a substantially continuous liquid layer on the core material particles, (viii) then allowing the thus applied continuous coating layer on the particles to at least partially dry by contact with the drying gas, and (ix) withdrawing the coated particles from the spray-drying chamber.

32. The method according to claim 31 wherein the flow of the transport gas with the particles of the carrier material dispersed therein and the flow of the drying gas are directed substantially parallel to each other and are regulated so that they form a substantially distinct interface of a substantially constant shape in a region upstream and adjacent to the region where the collision between the liquid droplets and the particles takes place.

33. The method according to claim 31 or 32 wherein only partial solidification of the continuous coating layer in the spray-drying chamber is performed, so the particles form loose agglomerates collected on a bed of an air-penetrable material and are further dried on the bed.

34. The method according to claim 31 wherein the iron is provided as an organic iron compound.

35. The method according to claim 34 wherein the organic iron compound is selected from the group consisting of a fumarate, an acetate, a glutamate, a succinate, a formate, a lactate, a dextran, a propionate, a fatty acid salt of iron, an amino acid salt of iron, and a mixture thereof.

36. The method according to claim 31 wherein the iron is provided in the form of organic iron compound particles of an average size which is at the most 50 μm.

37. The method according to claim 36 wherein the organic iron compound particles have an average size which is at the most 30 μm, preferably at the most 10 μm.

38. The method according to claim 31 wherein the partially hydrolyzed protein has a degree of hydrolysis which is at least 5%.

39. The method according to claim 38 wherein the partially hydrolyzed protein is partially hydrolyzed haemoglobin.

40. The method according to claim 31 wherein the content of the amino acid-containing ingredient is in the range of 5 to 30 wt %.

41. The method according to claim 31 wherein the coating composition further comprises a fatty acid-containing substance selected from the group consisting of rendered lard, milk fat, tallow, a vegetable oil, and a marine animal oil in an amount which is in the range of 1 to 50 wt %.

42. The method according to claim 41 wherein the amount of the fatty acid-containing substance is in the range of 5 to 20 wt %.

43. The method according to claim 31 wherein the coating composition comprises an emulsified mixture of the amino acid-containing ingredient and a fatty acid-containing substance, said fatty acid-containing substance being selected from the group consisting of rendered lard, milk fat, tallow, a vegetable oil and a marine animal oil.

44. The method according to claim 31 wherein the inner core comprises a dietary fiber selected from the group consisting of a pectin, a carrageenan, a vegetable gum, a microbially derived gum, and an alginate.

45. The method according to claim 44 wherein at least 50% of the dietary fiber is water soluble.

46. The method according to claim 44 wherein the content of the dietary fiber in the inner core material in the range of 1 to 50 wt %.

47. The method according to claim 46 wherein the content of the dietary fiber in the inner core material is in the range of 5 to 30 wt %.

48. The method according to claim 34 wherein the inner core material further comprises a mixture of a dietary fiber selected from the group consisting of a pectin, a carrageenan, a vegetable gum, a microbially derived gum, and an alginate.

49. The method according to claim 31 wherein the weight ratio between the coating layer and the inner core is in the range of 10:90 to 99:1.

50. The method according to claim 49 wherein the weight ratio is in the range of 20:80 to 60:40.

51. A method of dietetically supplying iron to an individual suffering from anaemia, comprising administering to said individual the composition as defined in claim 1 in an amount and for a period of time which results in a concentration of at least 90 grams per liter of haemoglobin in the blood of the individual.

52. A method according to claim 51 wherein the individual is a suckling piglet.

53. A method according to claim 52 wherein the composition is administered over a period of two weeks in a total amount of at the most 35 g.

54. A method according to claim 51 wherein the composition is administered by voluntary ingestion by the individual.

55. A composition according to claim 7 wherein the organic iron compound particles have an average size which is at the most 10 μm.

* * * * *

UNITED STATES PATENT AND TRADEMARK OFFICE
CERTIFICATE OF CORRECTION

Page 1 of 2

PATENT NO. : 5,662,922

DATED : September 2, 1997

INVENTOR(S) : Christensen

It is certified that error appears in the above-identified patent and that said Letters Patent is hereby corrected as shown below:

Col. 2, line 50, delete "to", before "providing the"

Col. 10, line 22, "liquid-droplets" should be -- liquid droplets --.

Col. 10, line 34, delete "oath" and insert -- path --;

Col. 10, line 34, there should be a ")" after the word --downstream--

Col. 14, line 40, "rotation-Symmetrical" should be -- rotation-symmetrical --.

Col. 14, line 57, "Spray-cooling" should be -- spray-cooling --.

Col. 18, before line 54, insert --3) Biopect™ is a powdered pectin-containing product consisting of the following ingredients: 20 wt% of dried potato pulp, 54 wt% of dried apple pomace, 5 wt% of citrus pulp, 10 wt% of carrageenan, 10 wt% of Psyllium seeds and 1 wt% of betaine hydrochloride. The product particles have an average size of about 50 $\mu$m (in the range of 10 $\mu$m to 100 $\mu$m)--.

UNITED STATES PATENT AND TRADEMARK OFFICE
CERTIFICATE OF CORRECTION

PATENT NO. : 5,662,922

DATED : September 2, 1997

INVENTOR(S) : Christensen

It is certified that error appears in the above-identified patent and that said Letters Patent is hereby corrected as shown below:

Col. 20, line 13, delete "af" and insert -- of --.

Col. 20, line 47, insert -- in the trial --.

Signed and Sealed this

Thirtieth Day of June, 1998

Attest:

BRUCE LEHMAN

*Attesting Officer*     *Commissioner of Patents and Trademarks*